United States Patent [19]

Titball et al.

[11] Patent Number: 5,817,317
[45] Date of Patent: Oct. 6, 1998

[54] CLOSTRIDIUM PERFRINGENS VACCINES

[75] Inventors: Richard William Titball; Ethel Diane Williamson, both of Salisbury, England

[73] Assignee: The Secretary of State for Defense of Great Britian & Northern Ireland, London, England

[21] Appl. No.: 341,538

[22] PCT Filed: May 20, 1993

[86] PCT No.: PCT/GB93/01039

§ 371 Date: Nov. 28, 1994

§ 102(e) Date: Nov. 28, 1994

[87] PCT Pub. No.: WO93/23543

PCT Pub. Date: Nov. 25, 1993

[30] Foreign Application Priority Data

May 20, 1992 [GB] United Kingdom .................. 9210717
Jul. 23, 1992 [GB] United Kingdom .................. 9215655

[51] Int. Cl.$^6$ .......................... A61K 39/08; C07K 14/33
[52] U.S. Cl. .................................. 424/190.1; 424/192.1; 424/197.11; 424/239.1; 435/69.3; 436/544; 436/545; 436/546; 530/324; 530/402; 530/412; 530/825
[58] Field of Search .......................... 435/69.3; 530/324, 530/825, 402, 412; 424/239.1, 190.1, 192.1, 197.11

[56] References Cited

U.S. PATENT DOCUMENTS 4,877,612 10/1989 Berger et al. .
5,200,318 4/1993 Rabin et al. .

OTHER PUBLICATIONS

Logan et al. Infection and Immunity 59(12):4338–4342, Dec. 1991.

Titball et al. Infection and Imunity 57(2): 367–376, Feb. 1989.

Titball et al., Hemolytic and Sphingomyelinase Activities of Clostridium perfringens Alpha–Toxin Are Dependent on a Domain Homologous to That of an Enzyme from the Human Arachidonic Acid Pathway, Infection and Immunity 59, 1872–1874 (1991). See entire article.

Basic & Clinical Immunology, H. Fudenberg et al. eds., Lange Medical Publications 1980. see ch. 44 pp. 722–736.

Primary Examiner—Anthony C. Caputa
Attorney, Agent, or Firm—Nixon & Vanderhye

[57] ABSTRACT

The present invention provides novel peptides and vaccines containing them capable of inducing production of antibodies directed against *Clostridium perfringens* alpha-toxin (CPa) in animals to which they are administered and thereby providing prophylaxis against infection by *Clostridium perfringens* and/or the alpha-toxin itself. Particularly the present invention provides such a vaccine that is relatively safe and simple to produce. e.g. by genetic engineering means. Preferred peptides comprise theo amino acid sequence of *Clostridium perfringens* alpha-toxin from amino acid 247 to 370 but lack the epitopes necessary for phospholipase C and/or sphingomyelin hydrolysing activity found between amino acids 1 to 240 of that sequence. Further provided are antisera and antibodies raised to the peptides and vaccines of the present invention, and particularly monoclonal antibodies and hybridoma cell lines for their production.

14 Claims, 2 Drawing Sheets

CLOSTRIDIUM PERFRINGENS VACCINES

The present invention relates to novel peptides capable of illiciting an immunological response that is protective against *Clostridium perfringens* in man or animals; more particularly to novel peptides capable of illiciting such protective response against the alpha-toxin of that organism, and antibodies and antisera raised thereto. Preferred agents enable prophylaxis and treatment of *Clostridium perfringens* induced disease states in both humans and other animals.

*Clostridium perfringens* (*C. perfringens*) is ubiquitous in the environment and has been found in the soil, decaying organic matter and as part of the gut flora in man and animals. Different strains of *C. perfringens* can be assigned to one of five biotypes (A–E) depending on the spectrum of toxins produced (McDonel (1986) Pharmacology of Bacterial Toxins; F Dorner and J Drews (Editors) Pergamon Press, Oxford). Biotype A strains are of particular importance as the etiological agents of gas gangrene in man. The disease is of increasing significance in the elderly and in diabetic populations, especially in those who have undergone lower limb surgery, where impaired blood supply to tissues can lead to anoxic conditions suitable for multiplication of the bacterium. The disease can also arise in patients who have undergone surgery of the gastrointestinal tract when contamination of damaged tissues with gut contents can result in its establishment. A more periodic increase in the incidence of gas gangrene has been shown to occur during armed conflicts when deep tissue wounds are contaminated with soil and the failure to promptly treat such injuries resulted in the death of several hundred thousand combatants during World War I.

The pathogenesis of gas gangrene can be largely attributed to the production of potent exotoxins by the bacterium, of which the alpha-toxin has received attention as the major contributor to the disease. The toxin may act peripherally to the initial focus of infection by damaging and reducing the blood supply to tissues thus promoting the conditions required for spread of the infection.

In the later stages of the disease the toxin may act sytemically causing death. A crude *C. perfringens* toxoid vaccine was demonstrated to provide protection against experimentally induced gas gangrene as long ago as 1937 (Penfold and Tolhurst (1937) Medical Journal of Australia, pp 604)) and subsequent studies suggested that the effective component of this vaccine was derived from the alpha-toxin ( Robertson and Keppie (1943), Lancet 2 p311; Boyd et al (1972) J. Med. Microbiol 5, p467; Kameyama (1975) Japanese Journal of Medicine, Science and Biology 25, p200). In spite of these advances a vaccine has not been developed for use in humans and current treatment for gas gangrene usually involves the removal of the affected limb or tissues.

*C. perfringens* has also been identified, or implicated, as the causative agent of other diseases, for example in colic and enterotoxaemia, in horses, rabbit, cattle, sheep and poultry. Vaccines for use in such animals have been described in a number of prior patent applications, eg U.S. Pat. No. 4,2654,588, U.S. Pat. No. 4,292,307, GB 2030451, SU 152943, GB 968199, GB 958575, GB 958574 and GB 958564; all being formal toxoids or equivalents.

The present inventors have previously isolated the gene encoding the alpha-toxin ( Titball et al (1989) Infection and Immunity, Vol 57, p357–376) and examined structure-function relationships of the protein (Titball and Rubidge 1990; Titball et al (1991) Infection and Immunity, Vol 59, p1872–1874). As part of these studies the location of some antibody epitopes were determined (Logan et al (1992) Infection and Immunity, Vol 59, p4338–4382).

It is an object of the present invention to provide novel vaccines capable of inducing production of protective antibodies directed against *C. perfringens* alpha-toxin (CPa) when administered to animals or man and thereby providing prophylaxis against infection by *C. perfringens*, disease states resulting from such infection, and/or the alpha-toxin itself. It is a particular aim of the present invention to provide such a vaccine that is relatively safe and simple to produce. Antibodies and antisera so raised are also provided capable of use in therapy for at least some, if not all, disease states, where alpha toxin is essential for the organisms effect or viability.

A further object of the present invention is to provide isolated vaccine peptides and conjugates capable of inducing production of antibodies to CPa such that they might also be used as tools to study the role of the alpha-toxin in the pathogenesis of gas gangrene; such vaccine peptides being free of other toxoided *C. perfringens* activity. In order to achieve these objects the present inventors have provided novel peptides capable of being used in such vaccines as the active immunising agent or agents.

Thus in its broadest embodiment the present invention provides a peptide or peptide conjugate comprising the amino acid sequence of epitopes of *C. perfringens* alpha-toxin from amino acid 261 to 300 but lacking epitopes/amino acid sequences necessary for phospholipase C and/or sphingomyelin hydrolysing activity that are found between amino acids 1 to 240 of the alpha-toxin; said peptide being capable of inducing an immune response protective against the alpha-toxin when administered to humans or animals. Titball et al (1991) broadly describes the unwanted regions.

Preferably the peptides of the present invention comprise the amino acid sequence of *C. perfringens* alpha-toxin from amino acid 261 to amino acid 370; most preferably from 247 to 370. Particularly provided are such peptides as derived from *C. perfringens* Biotype A alphatoxin DNA.

In a most preferred form the peptides of the present invention consist of only amino acid 247 to amino acid 370 of the amino acid sequence of *C. perfringens* alpha-toxin or that amino acid sequence in the form of a fusion peptide with another amino acid sequence, that not being that of amino acid 1 to amino acid 246 of the alpha-toxin, or in the form of a conjugate with an agent having other desired effect. The term 'other amino acid sequence' will be understood by the person skilled in the art to include complete proteins as well as relatively short sequences as appropriate to the needs of the user. For example a non-*C. perfringens* antigenic protein may be included fused to the aforesaid sequence for the purpose of providing other immunity or labelling.

In a further embodiment the present invention provides vaccine compositions comprising suitable doses of the peptides or conjugates of the present invention, these being optionally complemented as necessary by further agents for optimising protection, eg. adjuvants and carriers. Some such suitable agents will be those as disclosed in the patents referred to on page 2. Freunds incomplete or complete adjuvant may be used as typical adjuvants, but other suitable candidates such as those described in WO 9203164 will occur to those skilled in the art. Carrier function may be fulfilled merely by saline solutions.

The present inventors and coworkers have determined that the neither the N-terminal (amino acids 1–249=$Cpa_{249}$) nor C-terminal (amino acids 250–370) domains are capable of lethal effect on their own. This is surprising in the light of findings that the phospholipase activity was found to be entirely present in the N-terminal domain while known sphingomyelinase related epitopes were found to be lacking in the sequence of the C-terminal domain. Further experimentation by these workers has showed that the N-terminal domain on its own is not capable of inducing a protective response in spite of the fact that antibodies directed at these N-terminal domain epitopes can neutralise the effects of the toxin. Thus it may readily be seen that the finding that the relatively inactive C-terminal domain can illicit a protective response where the relatively active N-terminal cannot is an entirely surprising result.

The positions of C-terminal epitopes have been mapped previously by the present inventors and their coworkers and found to lie at approximately position 273–275 and 295–297 in the alpha-toxin amino acid sequence. It is to be expected that the position or nature of these epitopes might vary slightly from isolate to isolate while maintaining functional activity and thus such variation are included in the scope of the invention where a protective response is retained.

It will be clear to a worker skilled in the art from the aforesaid disclosure that certain sequences within the C-terminal domain will be far more effective than others in providing the necessary immunogenic activity. This is because the protective effect is typically somewhat dependent upon the tertiary arrangement of the peptide in orienting the epitopes of interest to each other. This is further evidenced by the fact that the active epitope holding N-terminal domain is not lethal on its own, indicating that the C-terminal is necessary for correct orientation of these epitopes also. It is also clear that given the information herein the skilled worker will be able to screen the various sequences of the invention for necessary activity and that these various sequences may readily be provided using standard genetic engineering techniques such as polymerase chain reaction and gene cloning to provide sequences lacking the unwanted phospholipase and sphingomyelitical activity. These 'unwanted' regions are described in detail in papers by the present authors and coworkers (Shuttleworth et al (1988) 'Epitope mapping of *Clostridium perfringens* alpha-toxin' in F J Fehrenbach et al (Editors) bacterial Protein Toxins, Gustav Fischer Verlag. Stuttgart, p 65–66. Titball et al (1989) Infection and Immunity, Vol 57, p357–376; Titball et al (1991) Infection and Immunity, Vol 59. i, p1872–1874; Logan et al (1991) Infection and Immunity, Vol 59. 12. p 4338–4382).

In further aspects of the present invention there is provided recombinant DNA encoding for the peptides of the invention, plasmids comprising such DNA and cell lines comprising these plasmids or the recombinant DNA itself such that expression of the peptides may be achieved. Such recombinant DNA is conveniently provided by PCR amplification of the DNA encoding for the desired sequence, eg. $Cpa_{247-370}$ or $Cpa_{261-370}$, using primers targeted at respective ends of the double stranded sequence of which it forms one half. Alternatively suitable restriction enzymes might be used on larger quantities of native alpha-toxin encoding DNA. The derived DNA is ligated into a suitable vector, optionally contiguously running with a sequence comprising the remainder of a desired fusion peptide, and the vector inserted into a suitable host cell eg. such as *E. coli*. A desired peptide expressing cell line may be selected in the known way, eg. by Western Blotting using antibodies directed at the peptide, alpha toxin or a conjugated peptide such as GST.

It should be noted that selection of certain fusion peptides may facilitate isolation of the peptide by provision of a relatively large fraction which can be cleaved to yield the alpha-toxin related peptide after initial purification.

In a further aspect of the present invention there are provided antisera raised to the peptides of the invention and antibodies derived therefrom. Furthermore, the present invention provides monoclonal antibodies to the peptides of the invention and hybridoma cells for production thereof.

The antisera of the invention are readily prepared by injecting a host animal (eg. a mouse, pig or rabbit) with a peptide of the invention and then isolating serum from it after a waiting suitable period for antibody production, eg. 14 to 28 days. Antibodies may be isolated from the blood of the animal or its sera by use of any suitable known method, eg. by affinity chromatography using immobilised peptides of the invention or the peptides they are conjugated to, eg. GST, to retain the antibodies. Similarly monoclonal antibodies may be readily prepared using known procedures to produce hybridoma cell lines expressing antibodies to peptides of the invention. Such monoclonals antibodies may also be humanised eg. using further known procedures which incorporate mouse monoclonal antibody light chains from antibodies raised to the peptides of the present invention with human antibody heavy chains.

In order to assist the skilled worker there are now provided Figures and illustrative examples of peptides and peptide vaccines of the present invention. These are intended as non-limiting examples for provision of data regarding the efficacy of the basic C-terminal domain peptides from which skilled workers may draw their own conclusions regarding possible variations within the scope of the invention.

Sequence Listing

Figure 1:
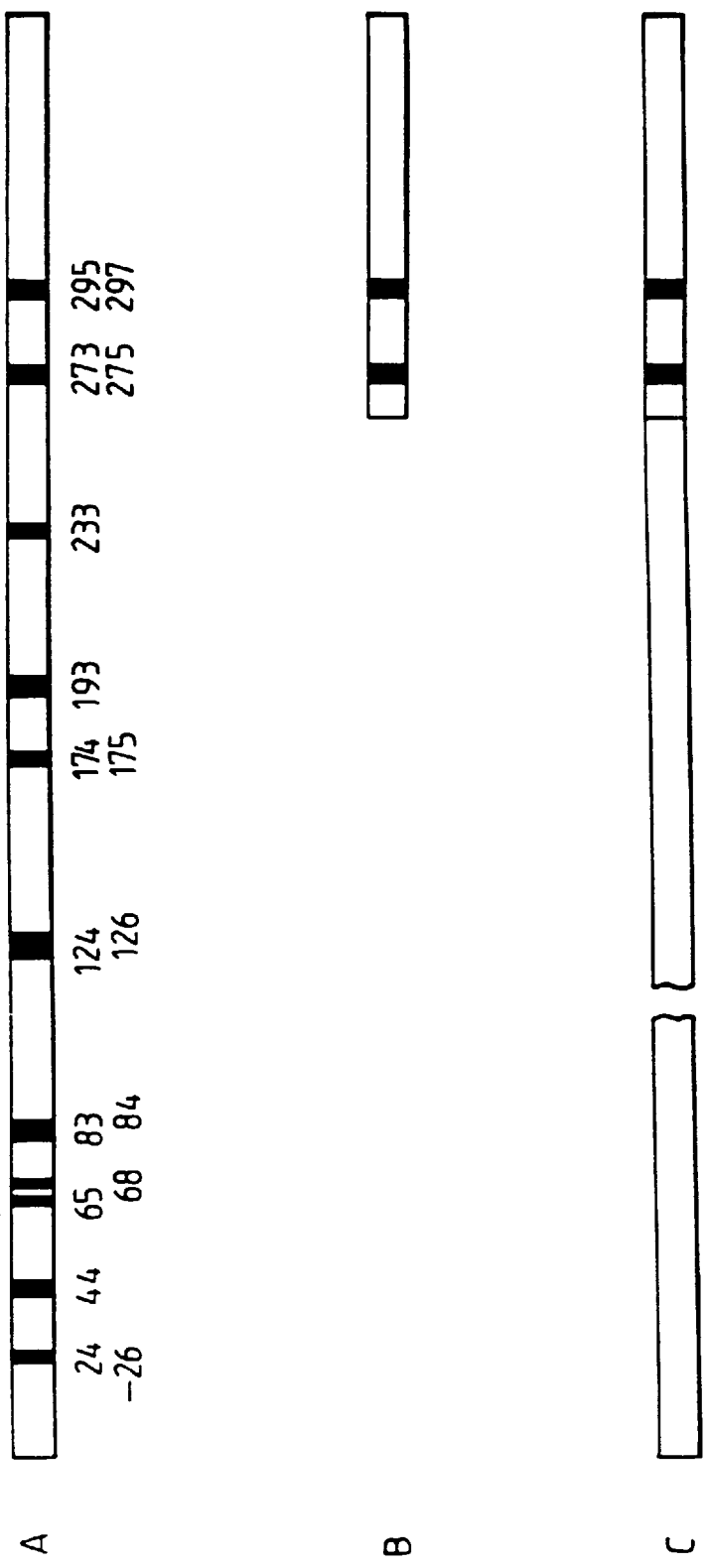
FIGS. 1A–C: shows the relative positions of major epitopes mapped on the complete alpha-toxin sequence ($Cpa_{1-370}$)=A; a C-terminal domain peptide of the invention ($Cpa_{247-370}$)=B and a fusion peptide of the invention (GST-$Cpa_{247-370}$)=C. Numbers indicate the approximate positions of the epitope.

SEQ ID No 1: is the complete DNA sequence coding for the *C. perfringens* alpha-toxin; this being one strand of the double stranded sequence.

SEQ ID No 2: is the amino acid sequence of alpha-toxin encoded by SEQ ID No 1.

SEQ ID No 3: is the DNA sequence coding for $Cpa_{247-370}$; the preferred peptide of the invention that has been identified herein.

SEQ ID No 4: is the amino acid sequence of $Cpa_{247-370}$.

EXAMPLES

Example 1: Generation of C-terminal (Cpa247–370) peptide of alpha-toxin of *C. perfringens* and its conjugates.

All chemicals were obtained from BDH Chemical Company or the Sigma Chemical Company unless otherwise stated. Vaccine peptide against the alpha-toxin of *C. perfringens* was generated by expressing, in *Escherichia coli*, a fragment of the alpha-toxin gene which would encode the C-terminal domain of the alpha-toxin (amino acids 247–370=$Cpa_{247-370}$).

The fragment of the alpha-toxin gene was generated by polymerase chain reaction (PCR) amplification of the region between nucleotides 823 and 1194 of the alpha-toxin gene sequence previously reported by Titball et al. Oligonucleotides (30-mers) were designed from the nucleotide sequence of the alpha-toxin gene (Cpa) of *C. perfringens* NCTC 8237 (see Titball et al (1989) Infect. Immun. 52, 367–376) synthesised on a Biosystems 392 DNA Synthesiser with 6 additional nucleotides at the 5' ends containing restriction endonuclease sites; the PCR primer homologous with the region starting at nucleotide 823 incorporated a nucleotide tail (GGG ATG) to facilitate cloning and expression of the gene fragment. The NCTC 8237 Cpa was cloned into a plasmid (as Titball; ibid) linearised and used as template DNA (40 ng) in the PCR. A DNA fragment encoding the $Cpa_{247-370}$ was produced as product after 20 amplification cycles (LEP Prem thermal cycler) purified by agarose gel electrophoresis and digested with SmaI and HindIII, The purified fragment was ligated with SmaI-HindIII digested pBluescript SK+ (Stratagene) and transformed into *E. coli* JM109 cells (see method Hanahan (1985) DNA cloning; a practical approach Vol 1 (Glover Ed) pp 109–135, IRL Press, Oxford). The verification of the authenticity of the nucleotide sequence of the cloned fragment was carried out using routine methods ( Maniatis et al, 1989. Molecular cloning:a laboratory manual. Cold Spring Harbor Laboratory Press.). A recombinant plasmid was generated (pCTH1) for the sequencing and cloning work.

Expression was achieved by isolating the $Cpa_{247-370}$ encoding fragment (SmaI—Hind III fragment ) from the pBluescript clone using SmaI and HindIII, purifying it, blunt ending the HindIII site using Klenow fragment (Sambrook et al: Molecular Cloning-as above) and ligating this 2fragment with SmaI digested pGEX-3X expression vector DNA (LKB-Pharmacia Biotechnology). The resultant recombinant plasmid expressed $Cpa_{247-370}$ as a fusion protein with the vector encoded glutathione-S-transferase (=GST-$Cpa_{247-370}$) when transformed intgo. *E. coli* JM 109 (as Hanahan-above). Transformants were screened using PCR and a colony isolated containing the plasmid pGEX3-13 (also called pB3X13). Expressed protein was then purified according to the procedure suggested by the plasmid manufacturers for the purification of GST.

Nucleotide sequencing was carried out by generating single stranded DNA from cells containing pCTH1 by co-infecting the cells with the helper bacteriophage M13K07 (see Sambrook-Molecular cloning-as above) wherein single stranded DNA is purified and used for dideoxy -termination sequencing reactions using alpha$^{35}$S-dC7? and the reaction products are separated by electrophoresis and visualised by autoradiography.

Expression and purification of GST-$Cpa_{247-370}$ and $Cpa_{247-370}$:

Protocol 1: *E. coli* containing the plasmid pGEX3X-13 was cultured in 10×100l1 volumes of BHI broth in 250ml Erlenmeyer flasks at 37° C. with shaking at 150 rpm. Fusion protein expression, expressed from the tac promoter, was induced by addition of IPTG (1 mM final concentration) to cultures that had reached an $OD_{600}$ of 0.6. After a further 5 hours of growth the cells were harvested by centrifugation and resuspended in 3 ml of phosphate buffered saline (PBS. Oxoid), lysozyme solution (80 µl. 10 mg/ml) was added to the suspension and, after incubation (10 min, 22° C.) 30 µl of Triton X-100 was added. The cell suspension was frozen (−20° C.). thawed and sonicated for 12×30 seconds (Braun Sonicator, Maximum power. 25 mm probe) on ice. After centrifugation (10.000× g. 4° C.) the supernatant was mixed with 2ml of glutathione-sepharose gel (Pharamacia) previously washed three times with PBS+0.1% Triton X-100. The mixture was stirred for 18 hours at 4° C., packed into a chromatography column and the column washed with 20 ml PBS+0.1% Triton X-100 followed by 10 ml tris buffer (10 mM, pH to 8.0 with HCl) containing 5 mM reduced glutathione. Fractions collected (2 ml) were analysed for the presence of fusion protein by SDS-polyacrylamide gel electrophoresis (Pharmacia Phast System. 10–15% gradient gels) and staining with Coomasie Blue R250. To generate $Cpa_{247-370}$ the GST-$Cpa_{247-370}$ fusion protein (2 mg) was cleaved for 18 hours (22° C.) with factor X (BCL: 3 µg) according to the manufacturer's datasheet. The mixture was applied to a 1 ml minicolumn of glutathione sepharose and the column eluted with 3 ml PBS. Fractions (1 ml) were analysed for $Cpa_{247-370}$ as described above and SDS-polyacrylamide gel analysis showed that pure $Cpa_{247-370}$ was obtained.

Protocol 2: *E. coli* containing pGEX3X-13 was cultured in 1 litre of L-broth+ampicillin at 37° C. 150 rpm until the optical density of the respective culture (600 nm) was approximately 0.3. IPTG was added to a final concentration of 1 mM and the culture grown for a further 4 hrs. A total cell lysate was prepared by resuspending the cells in 30 ml PBS+tritonx100 (1%) and sonicated for 5 ×30 seconds on ice using a Braun Labsonic sonicator. The supernatant obtained after centrifugation was purified by selective elution from a column of glutathione-sepharose (LKB-Pharmacia). For isolation of the $Cpa_{247-370}$ fragment alone the GST-$Cpa_{247-370}$ peptide (approx 10 mg in 80 µl) was digested with factor X, (15 U) overnight at room temperature, and the $Cpa_{247-370}$ fragment separated from the GST by passage through a glutathione-sepharose column.

Immunological properties of $Cpa_{247-370}$

To establish whether isolated and purified C-terminal domain of $Cpa_{247-370}$ Was immunologically similar to that region of the complete alpha-toxin, it was used as an immunogen in mice, see below, and the resulting antiserum reacted with overlapping peptides derived from primary amino acid sequence in the C-terminal domain of the toxin. The results indicated that the pattern of reactivity did not differ from that obtained when antiserum to the whole toxin was reacted with these peptides (see method Logan et al (1991) Infect. Immun. 59. 4338–4342, suggesting that no new and significant sequential antibody binding regions were created and that correct folding and structure identity with the C-terminal in the complete toxin was present.

Biochemical properties of $Cpa_{247-370}$

Purified $Cpa_{247-370}$ was tested in a number of enzyme assays wherein it was determined that it lacked sphingomyelinase activity and did not cause haemolysis of mouse erythrocytes, as distinct from the complete toxin which exhibits these. As the folding has been shown to be the same it is considered that no coding for this activity is present.

Cellular effects

While (1.25 µg/ml alpha-toxin is toxic for mouse lymphocytes, rising to a dose response maxima at 2.5 µg/ml tissue culture volume and after 20 hours, neither $Cpa_{1-249}$ nor $Cpa_{247-370}$ were toxic at these concentrations; $Cpa_{247-370}$ not being toxic in 10 µg injections to mice whereas 1 µg alpha-toxin causes death within in 24 hours. However, when $Cpa_{1-249}$ and $Cpa_{247-370}$ were used together haemolyis of lymphocytes occured, but not when used sequentially. As *B. cereus* PC-$PCL_{1-249}$ and $Cpa_{247-370}$ do not have this effect it would appear that the two Cpa truncates interact to provide the enzymic effects.

| Biological Activity | peptide | amount | activity |
|---|---|---|---|
| PhospholipaseC | Cpa | 0.04 nmol | 0.079 U/min |
| pNPPChydrolysis[a] | $Cp_{247-370}$ | 0.94 nmol | <0.001 U/min |
| Sphingomyelinase | Cpa | 0.34 nmol | 1003 U/min |
| TNPALhydrolysis[b] | $Cp_{247-370}$ | 0.34 nmol | <0.01 U/min |
| Sphingomyelinase | Cpa | 0.06 nmol | hydrolysis |
| TLC assay[c] | $Cp_{247-370}$ | 0.17 nmol | no hydrolysis |
| Haemolytic[d] | Cpa | 0.017 nmol | 1.05 Hu/min |
| | $Cpa_{247-370}$ | 0.05 nmol | <0.007 Hu/min |

Cpa=alpha-toxin; $Cpa_{247-370}$=preferred truncate of the invention a=p-nitrophenolphosphorylcholine(pNPPC) hydrolysing activity 1 U catalysed hydrolysis of 1 nmol of substrate.
b = N-omega-trinitrophenyllaurylsphingosylphosphorylcholine (TNPAL) hydrolysing activity. 1 U catalysed hydrolysis of 1 nmol substrate
c=Hydrolysis of bovine brain or erythrocyte or chicken egg yolk sphingomyelin assessed by TLC.
d=Haemolytic activity. 1 Haemolytic unit (Hu) caused 50% lysis of 100 µl of a 5% v/v mouse erythrocyte suspension.

Toxicity of candidate vaccines

Barrier-bred female 6-week old Balb/cmice, free of mouse pathogens, were obtained from Charles River Laboratories, Margate, Kent UK, and wre used throughout these studies.

The toxicity of the vaccine fusion peptide was determined by intra-peritoneal inoculation of 10 µg amounts into a groups of 6 mice. The vaccine was non-lethal at these doses and mice showed no signs of acute or chronic toxicity for up to two weeks post inoculation.

Antibody responses to vaccines

Figure 2:
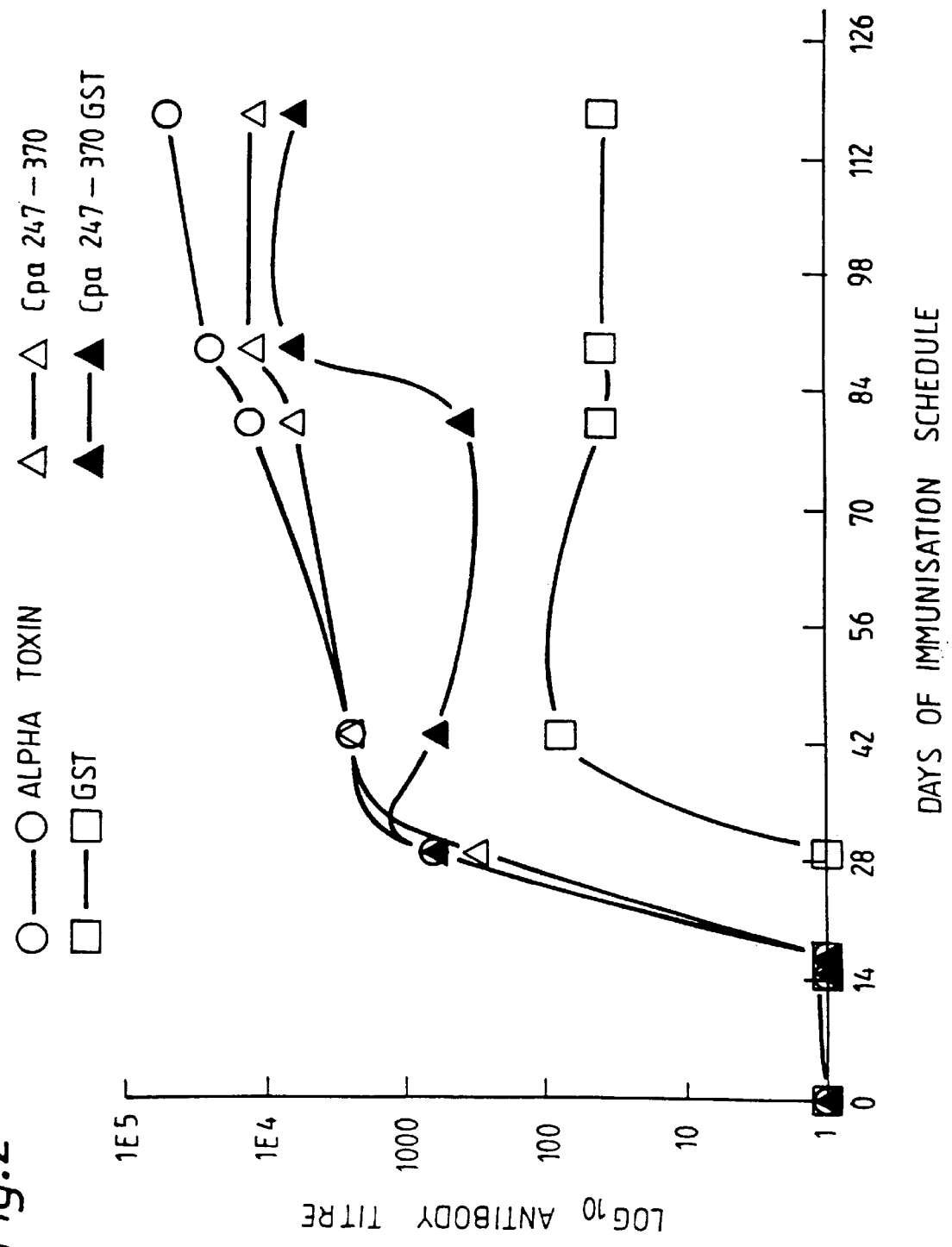
FIG. 2.: shows the $\log_{10}$ antibody titre v days after initial injection (i.p.) with test vaccines. Booster injections are indicated by anotation ⁻ on the x plot. Titres are independent of protection. O=alphatoxin; Square=GST; Triangles-open= $Cpa_{247-370}$;–closed=$Cpa_{247-370}$GST.

The candidate vaccines were administered to groups of 6 mice by intra-peritoneal inoculation with adjuvant (Incomplete Freunds Adjuvant-IFA). The appearance of antibody against the alpha-toxin was monitored by ELISA. $Cpa_{247-370}$ or GST-$Cpa_{247-370}$ induced a strong antibody response against the alpha-toxin which increased after booster inoculations (FIG. 2). The alpha-toxin antibody response against $Cpa_{247-370}$ was not affected by the fusion of this polypeptide with glutathione-S-transerfase. The magnitude of the antibody response against $Cpa_{249}$ (N-terminal domain). $Cpa_{247-370}$ or GST-$Cpa_{247-370}$ was similar to that observed when a crude formaldehyde alpha-toxoid was administered.

Properties of antibodies raised against vaccines

The ability of serum from animals immunised with $Cpa_{249}$, $Cpa_{247-370}$ or GST-$Cpa_{247-370}$ to neutralise, in vitro, biological activities associated with the alpha-toxin was investigated. All effectively inhibited the phospholipase C activity of the toxin; however only antiserum generated against $Cpa_{247-370}$ or $GSTCpa_{247-370}$ inhibited the haemolytic activity of the toxin.

Protection against toxin challenge

Animals which were immunised with formol-toxoid, $Cpa_{249}$, $Cpa_{247-370}$, GST-$Cpa_{247-370}$ or GST alone were challenged intraperitonally with 5 µg of purified alpha-toxin ( approximately 50 $LD_{50}$ doses ). Control mice and mice immunised with GST died within 24 hr and 4 of 6 mice immunised with $Cpa_{249}$ died during this time. Mice immunised with the formal-toxoid, $Cpa_{247-370}$ or GST-$Cpa_{247-370}$ survived and showed no signs of intoxication.

Protection Against Organism Challenge

To investigate the possibility that the formol-toxoid, Cpa247–370 or GST-$Cpa_{247-370}$ could also induce protection against experimental gas-gangrene, groups of six mice, which had been immunised with these candidate vaccines, were challenged intramuscularly with $10^{10}$ viable cells of C. perfringens NCTC 8237. All of the immunised animals survived this challenge whereas 3/6 control animals which had not been immunised died with 48 hrs.

TABLE 2: Protection against challenge with alpha-toxin afforded by immunisation with candidate vaccines. Groups of six Balb/C mice received 6×10 µg intraperitoneal doses of antigen mixed with Freunds incomplete adjuvant over a period of 80 days. The mice were challenged intraperitoneally with 10 µg of purified alpha-toxin and deaths recorded up to 24 hr.

| Antigen | Challenge with alpha-toxin | |
|---|---|---|
| | dose (µg) | survivors |
| none | 10 | 0/6 |
| formol toxoid | 10 | 6/6 |
| $Cpa_{247-370}$ | 10 | 6/6 |
| GST-$Cpa_{247-370}$ | 10 | 6/6 |

Conclusions

The most easily genetically engineered vaccine generated during this study, $Cpa_{247-370}$ represents the C-terminal domain of the alpha-toxin. This protein appears to be non-toxic in the mouse in doses up to 10 µg. The repeated inoculation of mice with this protein induced a strong antibody response which protects animals against the alpha-toxin and against challenge with C. perfringens. This vaccine offers several potential advantages over the formol-toxoid: it is much more easily prepared and because it is free from formaldehyde, other toxoided C. perfringens toxins and partially toxoided materials it is inherently safer for vaccine application and less reactogenic.

COMPARATIVE EXAMPLES

A number of other vaccine candidates were prepared that encompassed a region of the alpha toxin recognised by a phospholipase-C neutralising antibody (this region being $Cpa_{193-198}$) with additional regions that might be required for correct presentation of this region, using models to ensure that complete helices would be included. A BamH1-HindIII fragment from Cpa encoding a 20.5 kDalton (kDa) fragment of the protein containing six predicted helices was expressed as a cro-β-galactosidase (cro-β-gal-$Cpa_{99-249}$). A plasmid was also constructed encoding a 9 kDa fragment containing three predicted helices (cro-β-gal-$Cpa_{179-249}$). All were purified and this checked by SDS-PAGE. All proteins reacted with antibodies raised to neutralise the phospholipase C activity, but cro-β-galactosidase alone did not.

Neither of the $Cpa_{99-249}$ nor $Cpa_{179-249}$ produced a measurable antitoxin titre. $Cpa_{249}$ gave similar titre to the formol toxoid yet failed to prevent haemolytic activity in vitro and all alpha-toxin challenged animals died in in vivo tests. Only the formol toxoid and Cpa$_{247-370}$ peptide family immunised animals survived. It should be noted that the unconjugated peptide gave superior protection to GST-conjugate when $10^9$ viable *C. perfringens* cells were injected intramuscularly in 10 μl saline.

We claim:

1. A peptide comprising the amino acid sequence from amino acid 261 to amino acid 300 of *Clostridium perfringens* alpha toxin as set forth in SEQ ID NO:2, wherein said peptide lacks an amino acid sequence having phospholipase C and sphinogmyelin hydrolyzins activity and said peptide induces an immune response protective against the alpha-toxin when administered to humans or animals.

2. A peptide according to claim 1 comprising the amino acid sequence from amino acid 261 to amino acid 370 of *Clostridium perfringens* alpha toxin as set forth in SEQ ID NO:2, wherein said peptide lacks an amino acid sequence having phosphoplipase C and sphingomyelin hydrolyzing activity and said peptide induces an immune response protective against the alpha-toxin when administered to humans or animals.

3. A peptide according to claim 1 comprising the amino acid sequence from amino acid 247 to amino acid 370 of *Clostridium perfringens* alpha toxin as set forth in SEQ ID NO:2, wherein said peptide lacks an amino acid sequence having phosphoplipase C and sphingomyelin hydrolyzing activity and said peptide induces an immune response protective against the alpha-toxin when administered to humans or animals.

4. The peptide of claim 1, in the form of a fusion protein.

5. The peptide of claim 2 in the form of a fusion peptide.

6. The peptide of claim 3, in the form of a fusion protein.

7. The peptide of claim 4, wherein the fusion protein comprises the amino acid sequence of glutathione-S-transferase.

8. The peptide of claim 6, wherein the fusion protein comprises the amino acid sequence of glutathione-S-transferase.

9. The peptide of claim 4, wherein the fusion protein comprises an amino acid sequence for labeling or for immunity other than *Clostridium perfringens*.

10. The peptide of claim 4, wherein the fusion protein comprises a peptide which facilitates isolation.

11. The peptide as claimed in claim 1, which is expressed by a recombinant cell line.

12. A vaccine comprising the peptide of claim 1 and a pharmaceutically acceptable carrier.

13. A vaccine comprising the peptide of claim 2 and a pharmaceutically acceptable carrier.

14. A vaccine comprising the peptide of claim 3 and a pharmaceutically acceptable carrier.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1113 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Clostridium perfringens
        ( B ) STRAIN: double ( i x ) FEATURE:
        ( A ) NAME/KEY: CDS
        ( B ) LOCATION: 1..1110

( i x ) FEATURE:
        ( A ) NAME/KEY: CDS
        ( B ) LOCATION: 736..1110

( x i ) SEQUENCE DESCRIPTION: SEQ ID NO:1:

```
TGG GAT GGA AAG ATT GAT GGA ACA GGA ACT CAT GCT ATG ATT GTA ACT      48
Trp Asp Gly Lys Ile Asp Gly Thr Gly Thr His Ala Met Ile Val Thr
 1               5                  10                  15

CAA GGG GTT TCA ATC TTA GAA AAT GAT CTG TCC AAA AAT GAA CCA GAA      96
Gln Gly Val Ser Ile Leu Glu Asn Asp Leu Ser Lys Asn Glu Pro Glu
             20                  25                  30

AGT GTA AGA AAA AAC TTA GAG ATT TTA AAA GAG AAC ATG CAT GAG CTT     144
Ser Val Arg Lys Asn Leu Glu Ile Leu Lys Glu Asn Met His Glu Leu
         35                  40                  45

CAA TTA GGT TCT ACT TAT CCA GAT TAT GAT AAG AAT GCA TAT GAT CTA     192
Gln Leu Gly Ser Thr Tyr Pro Asp Tyr Asp Lys Asn Ala Tyr Asp Leu
     50                  55                  60

TAT CAA GAT CAT TTC TGG GAT CCT GAT ACA GAT AAT AAT TTC TCA AAG     240
Tyr Gln Asp His Phe Trp Asp Pro Asp Thr Asp Asn Asn Phe Ser Lys
 65                  70                  75                  80

GAT AAT AGT TGG TAT TTA GCT TAT TCT ATA CCT GAC ACA GGG GAA TCA     288
Asp Asn Ser Trp Tyr Leu Ala Tyr Ser Ile Pro Asp Thr Gly Glu Ser
                 85                  90                  95

CAA ATA AGA AAA TTT TCA GCA TTA GCT AGA TAT GAA TGG CAA AGA GGA     336
Gln Ile Arg Lys Phe Ser Ala Leu Ala Arg Tyr Glu Trp Gln Arg Gly
            100                 105                 110

AAC TAT AAA CAA GCT ACA TTC TAT CTT GGA GAG GCT ATG CAC TAT TTT     384
Asn Tyr Lys Gln Ala Thr Phe Tyr Leu Gly Glu Ala Met His Tyr Phe
        115                 120                 125

GGA GAT ATA GAT ACT CCA TAT CAT CCT GCT AAT GTT ACT GCC GTT GAT     432
Gly Asp Ile Asp Thr Pro Tyr His Pro Ala Asn Val Thr Ala Val Asp
    130                 135                 140

AGC GCA GGA CAT GTT AAG TTT GAG ACT TTT GCA GAG GAA AGA AAA GAA     480
Ser Ala Gly His Val Lys Phe Glu Thr Phe Ala Glu Glu Arg Lys Glu
145                 150                 155                 160
```

| | | | | | | | | | | | | | | | | |
|---|---|---|---|---|---|---|---|---|---|---|---|---|---|---|---|---|
|CAG|TAT|AAA|ATA|AAC|ACA|GCA|GGT|TGC|AAA|ACT|AAT|GAG|GCT|TTT|TAT|528|
|Gln|Tyr|Lys|Ile|Asn|Thr|Ala|Gly|Cys|Lys|Thr|Asn|Glu|Ala|Phe|Tyr||
| | | |165| | | |170| | | | |175| | | | |
|ACT|GAT|ATC|TTA|AAA|AAC|AAA|GAT|TTT|AAT|GCA|TGG|TCA|AAA|GAA|TAT|576|
|Thr|Asp|Ile|Leu|Lys|Asn|Lys|Asp|Phe|Asn|Ala|Trp|Ser|Lys|Glu|Tyr||
| | | |180| | | |185| | | | |190| | | | |
|GCA|AGA|GGT|TTT|GCT|AAA|ACA|GGA|AAA|TCA|ATA|TAC|TAT|AGT|CAT|GCT|624|
|Ala|Arg|Gly|Phe|Ala|Lys|Thr|Gly|Lys|Ser|Ile|Tyr|Tyr|Ser|His|Ala||
| | |195| | | | |200| | | | |205| | | | |
|AGC|ATG|AGT|CAT|AGT|TGG|GAT|GAT|TGG|GAT|TAT|GCA|GCA|AAG|GTA|ACT|672|
|Ser|Met|Ser|His|Ser|Trp|Asp|Asp|Trp|Asp|Tyr|Ala|Ala|Lys|Val|Thr||
| |210| | | | |215| | | | |220| | | | | |
|TTA|GCT|AAC|TCT|CAA|AAA|GGA|ACA|GCG|GGA|TAT|ATT|TAT|AGA|TTC|TTA|720|
|Leu|Ala|Asn|Ser|Gln|Lys|Gly|Thr|Ala|Gly|Tyr|Ile|Tyr|Arg|Phe|Leu||
|225| | | |230| | | | |235| | | | | |240| |
|CAC|GAT|GTA|TCA|GAG|GGT|AAT|GAT|CCA|TCA|GTT|GGA|AAG|AAT|GTA|AAA|768|
|His|Asp|Val|Ser|Glu|Gly|Asn|Asp|Pro|Ser|Val|Gly|Lys|Asn|Val|Lys||
| | | | |245| | | |250| | | | |255| | | |
|GAA|CTA|GTA|GCT|TAC|ATA|TCA|ACT|AGT|GGT|GAG|AAA|GAT|GCT|GGA|ACA|816|
|Glu|Leu|Val|Ala|Tyr|Ile|Ser|Thr|Ser|Gly|Glu|Lys|Asp|Ala|Gly|Thr||
| | | |260| | | | |265| | | | |270| | | |
|GAT|GAC|TAC|ATG|TAT|TTT|GGA|ATC|AAA|ACA|AAG|GAT|GGA|AAA|ACT|CAA|864|
|Asp|Asp|Tyr|Met|Tyr|Phe|Gly|Ile|Lys|Thr|Lys|Asp|Gly|Lys|Thr|Gln||
| | |275| | | | |280| | | | |285| | | | |
|GAA|TGG|GAA|ATG|GAC|AAC|CCA|GGA|AAT|GAT|TTT|ATG|ACT|GGA|AGT|AAA|912|
|Glu|Trp|Glu|Met|Asp|Asn|Pro|Gly|Asn|Asp|Phe|Met|Thr|Gly|Ser|Lys||
| |290| | | | |295| | | | |300| | | | | |
|GAC|ACT|TAT|ACT|TTC|AAA|TTA|AAA|GAT|GAA|AAT|CTA|AAA|ATT|GAT|GAT|960|
|Asp|Thr|Tyr|Thr|Phe|Lys|Leu|Lys|Asp|Glu|Asn|Leu|Lys|Ile|Asp|Asp||
|305| | | |310| | | | |315| | | | |320| | |
|ATA|CAA|AAT|ATG|TGG|ATT|AGA|AAA|AGA|AAA|TAT|ACA|GCA|TTC|TCA|GAT|1008|
|Ile|Gln|Asn|Met|Trp|Ile|Arg|Lys|Arg|Lys|Tyr|Thr|Ala|Phe|Ser|Asp||
| | | |325| | | | |330| | | | |335| | | |
|GCT|TAT|AAG|CCA|GAA|AAC|ATA|AAG|ATA|ATA|GCA|AAT|GGA|AAA|GTT|GTA|1056|
|Ala|Tyr|Lys|Pro|Glu|Asn|Ile|Lys|Ile|Ile|Ala|Asn|Gly|Lys|Val|Val||
| | | |340| | | |345| | | | |350| | | | |
|GTG|GAC|AAA|GAT|ATA|AAC|GAG|TGG|ATT|TCA|GGA|AAT|TCA|ACT|TAT|AAT|1104|
|Val|Asp|Lys|Asp|Ile|Asn|Glu|Trp|Ile|Ser|Gly|Asn|Ser|Thr|Tyr|Asn||
| | |355| | | | |360| | | | |365| | | | |
|ATA|AAA|TAA| | | | | | | | | | | | | |1113|
|Ile|Lys| | | | | | | | | | | | | | | |
| |370| | | | | | | | | | | | | | | |

( 2 ) INFORMATION FOR SEQ ID NO:2:

( i ) SEQUENCE CHARACTERISTICS:
        ( A ) LENGTH: 370 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Trp|Asp|Gly|Lys|Ile|Asp|Gly|Thr|Gly|Thr|His|Ala|Met|Ile|Val|Thr|
|1| | | |5| | | | |10| | | | |15|
|Gln|Gly|Val|Ser|Ile|Leu|Glu|Asn|Asp|Leu|Ser|Lys|Asn|Glu|Pro|Glu|
| | | |20| | | | |25| | | | |30| | |
|Ser|Val|Arg|Lys|Asn|Leu|Glu|Ile|Leu|Lys|Glu|Asn|Met|His|Glu|Leu|
| | |35| | | | |40| | | | |45| | | |
|Gln|Leu|Gly|Ser|Thr|Tyr|Pro|Asp|Tyr|Asp|Lys|Asn|Ala|Tyr|Asp|Leu|
| |50| | | | |55| | | | |60| | | | |

Tyr Gln Asp His Phe Trp Asp Pro Asp Thr Asp Asn Asn Phe Ser Lys
65              70                  75                  80

Asp Asn Ser Trp Tyr Leu Ala Tyr Ser Ile Pro Asp Thr Gly Glu Ser
            85                  90                  95

Gln Ile Arg Lys Phe Ser Ala Leu Ala Arg Tyr Glu Trp Gln Arg Gly
            100                 105                 110

Asn Tyr Lys Gln Ala Thr Phe Tyr Leu Gly Glu Ala Met His Tyr Phe
        115                 120                 125

Gly Asp Ile Asp Thr Pro Tyr His Pro Ala Asn Val Thr Ala Val Asp
    130                 135                 140

Ser Ala Gly His Val Lys Phe Glu Thr Phe Ala Glu Glu Arg Lys Glu
145                 150                 155                 160

Gln Tyr Lys Ile Asn Thr Ala Gly Cys Lys Thr Asn Glu Ala Phe Tyr
            165                 170                 175

Thr Asp Ile Leu Lys Asn Lys Asp Phe Asn Ala Trp Ser Lys Glu Tyr
            180                 185                 190

Ala Arg Gly Phe Ala Lys Thr Gly Lys Ser Ile Tyr Tyr Ser His Ala
        195                 200                 205

Ser Met Ser His Ser Trp Asp Asp Trp Asp Tyr Ala Ala Lys Val Thr
    210                 215                 220

Leu Ala Asn Ser Gln Lys Gly Thr Ala Gly Tyr Ile Tyr Arg Phe Leu
225                 230                 235                 240

His Asp Val Ser Glu Gly Asn Asp Pro Ser Val Gly Lys Asn Val Lys
            245                 250                 255

Glu Leu Val Ala Tyr Ile Ser Thr Ser Gly Glu Lys Asp Ala Gly Thr
            260                 265                 270

Asp Asp Tyr Met Tyr Phe Gly Ile Lys Thr Lys Asp Gly Lys Thr Gln
        275                 280                 285

Glu Trp Glu Met Asp Asn Pro Gly Asn Asp Phe Met Thr Gly Ser Lys
    290                 295                 300

Asp Thr Tyr Thr Phe Lys Leu Lys Asp Glu Asn Leu Lys Ile Asp Asp
305                 310                 315                 320

Ile Gln Asn Met Trp Ile Arg Lys Arg Lys Tyr Thr Ala Phe Ser Asp
            325                 330                 335

Ala Tyr Lys Pro Glu Asn Ile Lys Ile Ile Ala Asn Gly Lys Val Val
            340                 345                 350

Val Asp Lys Asp Ile Asn Glu Trp Ile Ser Gly Asn Ser Thr Tyr Asn
            355                 360                 365

Ile Lys
    370

( 2 ) INFORMATION FOR SEQ ID NO:3:

( i ) SEQUENCE CHARACTERISTICS:
        ( A ) LENGTH: 374 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Clostridium perfringens
        ( B ) STRAIN: double ( i x ) FEATURE:
    ( A ) NAME/KEY: CDS
    ( B ) LOCATION: 1..374

( x i ) SEQUENCE DESCRIPTION: SEQ ID NO:3:

```
AAT GAT CCA TCA GTT GGA AAG AAT GTA AAA GAA CTA GTA GCT TAC ATA      48
Asn Asp Pro Ser Val Gly Lys Asn Val Lys Glu Leu Val Ala Tyr Ile
 1           5                   10                  15

TCA ACT AGT GGT GAG AAA GAT GCT GGA ACA GAT GAC TAC ATG TAT TTT      96
Ser Thr Ser Gly Glu Lys Asp Ala Gly Thr Asp Asp Tyr Met Tyr Phe
             20                  25                  30

GGA ATC AAA ACA AAG GAT GGA AAA ACT CAA GAA TGG GAA ATG GAC AAC     144
Gly Ile Lys Thr Lys Asp Gly Lys Thr Gln Glu Trp Glu Met Asp Asn
         35                  40                  45

CCA GGA AAT GAT TTT ATG ACT GGA AGT AAA GAC ACT TAT ACT TTC AAA     192
Pro Gly Asn Asp Phe Met Thr Gly Ser Lys Asp Thr Tyr Thr Phe Lys
     50                  55                  60

TTA AAA GAT GAA AAT CTA AAA ATT GAT GAT ATA CAA AAT ATG TGG ATT     240
Leu Lys Asp Glu Asn Leu Lys Ile Asp Asp Ile Gln Asn Met Trp Ile
 65                  70                  75                  80

AGA AAA AGA AAA TAT ACA GCA TTC TCA GAT GCT TAT AAG CCA GAA AAC     288
Arg Lys Arg Lys Tyr Thr Ala Phe Ser Asp Ala Tyr Lys Pro Glu Asn
                 85                  90                  95

ATA AAG ATA ATA GCA AAT GGA AAA GTT GTA GTG GAC AAA GAT ATA AAC     336
Ile Lys Ile Ile Ala Asn Gly Lys Val Val Val Asp Lys Asp Ile Asn
             100                 105                 110

GAG TGG ATT TCA GGA AAT TCA ACT TAT AAT ATA AAA TA                  374
Glu Trp Ile Ser Gly Asn Ser Thr Tyr Asn Ile Lys
         115                 120             125
```

( 2 ) INFORMATION FOR SEQ ID NO:4:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asn Asp Pro Ser Val Gly Lys Asn Val Lys Glu Leu Val Ala Tyr Ile
 1           5                   10                  15

Ser Thr Ser Gly Glu Lys Asp Ala Gly Thr Asp Asp Tyr Met Tyr Phe
             20                  25                  30

Gly Ile Lys Thr Lys Asp Gly Lys Thr Gln Glu Trp Glu Met Asp Asn
         35                  40                  45

Pro Gly Asn Asp Phe Met Thr Gly Ser Lys Asp Thr Tyr Thr Phe Lys
     50                  55                  60

Leu Lys Asp Glu Asn Leu Lys Ile Asp Asp Ile Gln Asn Met Trp Ile
 65                  70                  75                  80

Arg Lys Arg Lys Tyr Thr Ala Phe Ser Asp Ala Tyr Lys Pro Glu Asn
                 85                  90                  95

Ile Lys Ile Ile Ala Asn Gly Lys Val Val Val Asp Lys Asp Ile Asn
             100                 105                 110

Glu Trp Ile Ser Gly Asn Ser Thr Tyr Asn Ile Lys
         115                 120
```